(12) United States Patent
Vannuffelen et al.

(10) Patent No.: US 7,675,030 B2
(45) Date of Patent: Mar. 9, 2010

(54) LOGGING SYSTEM AND METHOD FOR IN-SITU FLUIDS SENSING THROUGH OPTICAL FIBER WITH ATTENUATION COMPENSATION

(75) Inventors: Stephane Vannuffelen, Southampton (GB); Khalid Ouaaba, Sagamihara (JP); Tsutomu Yamate, Yokohama (JP)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

(21) Appl. No.: 11/855,144

(22) Filed: Sep. 13, 2007

(65) Prior Publication Data

US 2008/0087078 A1    Apr. 17, 2008

Related U.S. Application Data

(63) Continuation-in-part of application No. 11/273,893, filed on Nov. 14, 2005.

(60) Provisional application No. 60/825,722, filed on Sep. 15, 2006.

(51) Int. Cl.
*G01V 8/10* (2006.01)

(52) U.S. Cl. .................................. 250/269.1

(58) Field of Classification Search ............. 250/269.1; 359/236; 136/243
See application file for complete search history.

(56) References Cited

U.S. PATENT DOCUMENTS

| 4,241,997 A | 12/1980 | Chraplyvy |
| 5,535,293 A * | 7/1996 | Buchin ..................... 385/18 |
| 6,437,326 B1 | 8/2002 | Yamate et al. |
| 2004/0239923 A1* | 12/2004 | Adams et al. ............. 356/317 |
| 2007/0109537 A1 | 5/2007 | Vannuffelen et al. |

FOREIGN PATENT DOCUMENTS

| GB | 2368391 A | 5/2002 |
| JP | 56150332 A * | 11/1981 |
| JP | 06276702 A * | 9/1994 |
| WO | 2004/020774 A2 | 3/2004 |

* cited by examiner

*Primary Examiner*—Constantine Hannaher
(74) *Attorney, Agent, or Firm*—Matthias Abrell; Jaime Castano; Dale Gaudier

(57) ABSTRACT

A method for optically sampling characteristics of subsurface fluids within a wellhole using continuous, non-pulsed light transmitted downhole in optical fibers for both sampling and reference light channels for accurate attenuation compensation.

19 Claims, 9 Drawing Sheets

LOGGING SYSTEM AND METHOD FOR IN-SITU FLUIDS SENSING THROUGH OPTICAL FIBER WITH ATTENUATION COMPENSATION

CROSS-REFERENCE TO RELATED APPLICATION

This application relates to and claims the benefit under 35 U.S.C. §119(e) of applicants' U.S. Provisional Application Ser. No. 60/825,722 entitled "System and Method for Chemical Sensing Through Optical Fiber With Fiber Attenuation Compensation," filed Sep. 15, 2006. This application is a continuation-in-part of U.S. patent application Ser. No. 11/273,893 entitled "Real-Time Calibration for Downhole Spectrometer," filed Nov. 14, 2005. The disclosure of the aforementioned prior applications is hereby incorporated by reference as though set forth at length.

TECHNICAL FIELD

This invention relates to in-situ optical well logging of fluids within a wellhole. More specifically, this invention is directed to a method and system for directing light from an aboveground source through an optical fiber to a downhole sampling zone wherein characteristics of in-situ fluids (such as chemical composition, gas-oil ratios, and other physical properties) are determined by analytic means such as spectroscopy and wherein compensation for optical fiber attenuation is facilitated.

BACKGROUND OF THE INVENTION

Optical absorption spectroscopy systems and methods for use in downhole conditions are known and have been utilized in the oil industry for sensing physical and chemical properties of in-situ fluids. In particular, such logging tools are used for qualitative, e.g., contamination monitoring, or quantitative analysis, e.g., gas-oil ratio. Such methods include a source of light, a sampling cell, and a spectrometer located downhole.

Downhole environmental conditions, such as high temperature and pressure, impose constraints on the components involved in such methods, such as light sources and spectrometers. For example, a light source that can function in these harsh conditions is limited to a black-body type. Therefore, advantages may be achieved by removing both light source and processing aspects of optical spectrometers from downhole and locating them at the surface. A source of light located at the surface may be used to direct light through a single optical fiber. Such light may be modulated in the same manner as electrical signals and used to carry information as to the measured or detected characteristics of interest. The single fiber can also be used to retrieve light carrying such information from downhole to the surface where it can be processed through state-of-the-art instruments that can perform a spectral analysis.

In the past, use of optical fiber spectroscopy within a wellhole was disclosed in U.S. Pat. No. 6,437,326, of common assignment to Schlumberger Technology ("Schlumberger") with the present invention. The disclosure of this Schlumberger '326 patent is hereby incorporated by reference as though set forth at length.

As noted in the Schlumberger '326 patent, for spectroscopic applications, where it is important to have accurate determinations of the absorption of light in the sample itself, attenuation of the light traversing the optical fibers in the system must be considered and corrected. The '326 patent discloses use of a two-optical-fiber configuration, or a single-fiber configuration with Time Division Multiplexing (TDM) in order to compensate for this attenuation.

In a two-fiber configuration, one fiber is used for sample measurements and the other fiber is used as a reference to compensate for the attenuation in the system outside of the sample cell. However, in practice, the light paths for the sample and reference have different lengths, and such a configuration, therefore, leads to inaccuracies in the compensation for cable attenuation, which, in turn, adversely impacts the accuracy of the sample measurements. Additionally, a double-fiber configuration requires twice the length of fiber as a single-fiber configuration. In wells, which may typically involve depths of 25,000 feet or more, doubling the length of optical fiber substantially increases the overall cost of an operating system.

A TDM-based system requires a pulsed light source, which inherently reduces the optical power available for downhole system applications. Additionally, in systems where multi-sampling cells are employed, the demodulation of the light beams becomes a necessary but cumbersome step in processing optical signals to extract the measurement data. Although the above referenced Schlumberger '326 patent system is a significant advance in the art, room for worthwhile improvement remains.

SUMMARY OF THE INVENTION

In a preferred embodiment disclosed herein, a single fiber is utilized for both sampling and reference light beams, which facilitates more accurate attenuation compensation. Furthermore, systems disclosed herein are not limited to absorption measurements, but are more generally applicable to spectroscopic applications, including Raman photospectrometry. For example, light beams directed downhole can be used to trigger useful analytical in-situ phenomena that either lead to light emission (such as fluorescence) or to a change of light wavelength (a non-linear phenomenon).

Aspects of a system include (i) a light source located at the surface, (ii) an optical cable through which a source of light at the surface directs a beam of light downhole in a single optical fiber, (iii) a beam splitter located downhole that partitions the light beam within the optical cable into "M" independent reference channels and "K" independent sampling channels; each of which is associated with (iv) a sampling cell, (v) a modulator associated with said sampling cell, and (vi) a system for re-coupling the output of each of these channels. The re-coupled output light beam is then directed back through the single-fiber cable to the surface, to a detector capable of performing optical signal processing, and, based on the modulation schemes applied by the modulators, separating the re-coupled output beam into the individual channels for analysis using spectroscopy or other analytical techniques.

Further aspects include one or several modulator drivers connected to the cable and using the light carried by the cable as an energy source for their downhole operation.

The systems and methods of the subject invention are designed to provide in-situ sampling of fluids and conditions in wellholes and the determination of chemical and other characteristics of such fluids using continuous-energy light sources transmitted through an optical fiber. Such systems and methods result in convenient and more accurate attenuation compensation and, consequently, more accurate measurements of the characteristics under consideration.

A further aspect of the subject invention is the use of energy sources for operating the downhole systems of the subject invention and for other uses within the wellhole so as to reduce or eliminate the need to provide electrical power for the in-situ sampling of fluids and other characteristics within the wellhole.

THE DRAWINGS

Other aspects of the present invention will become apparent from the following detailed description of embodiments taken in conjunction with the accompanying drawings wherein.

Figure 8:
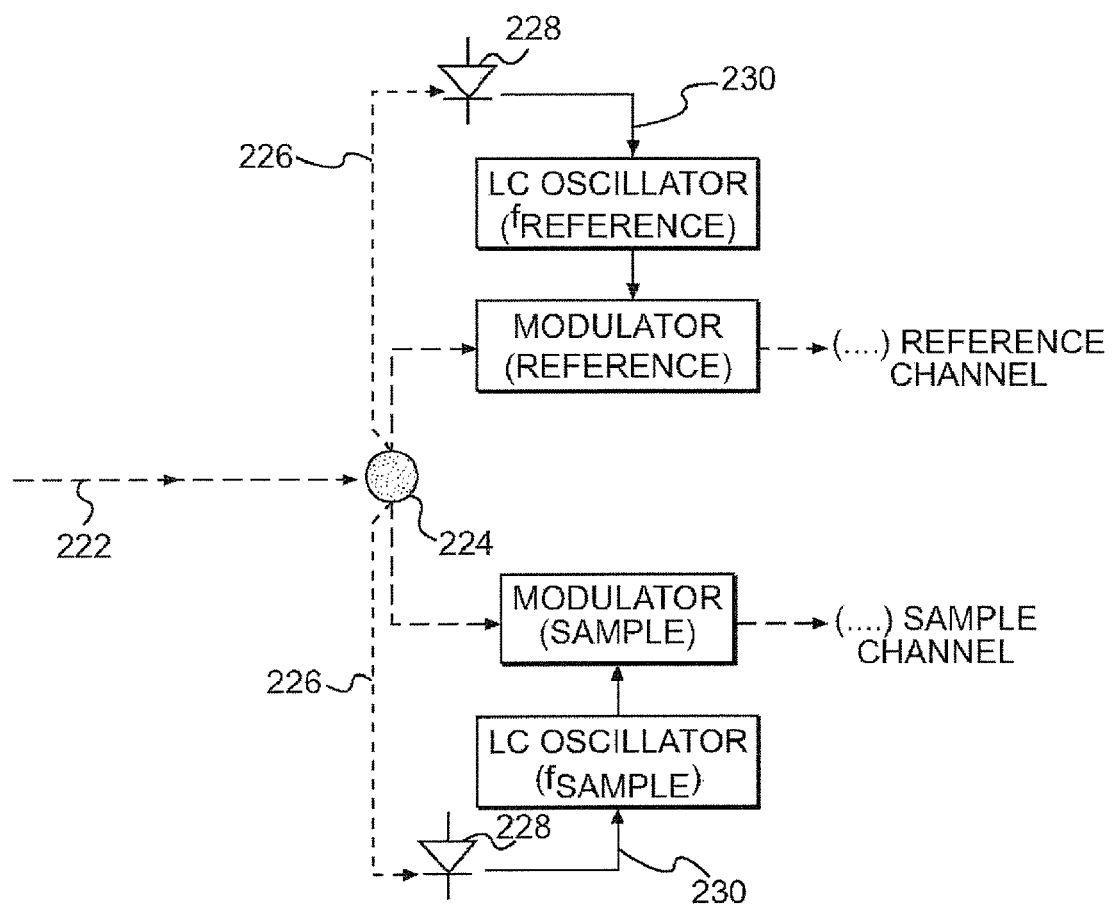

FIG. 8 discloses some examples of optical powering of modulators in an embodiment of the invention with one sampling channel and one reference channel.

Figure 9A:
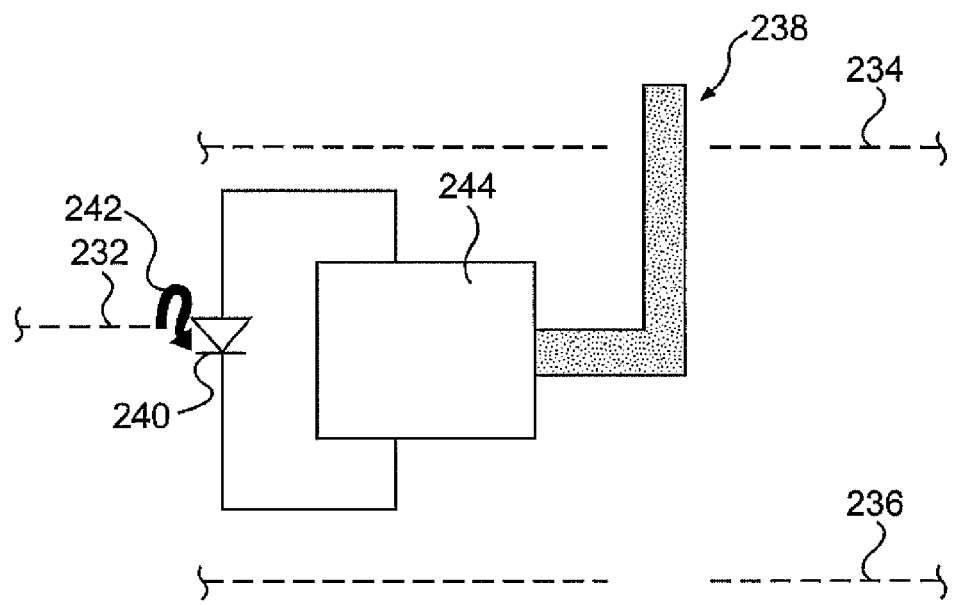
Figure 9B:
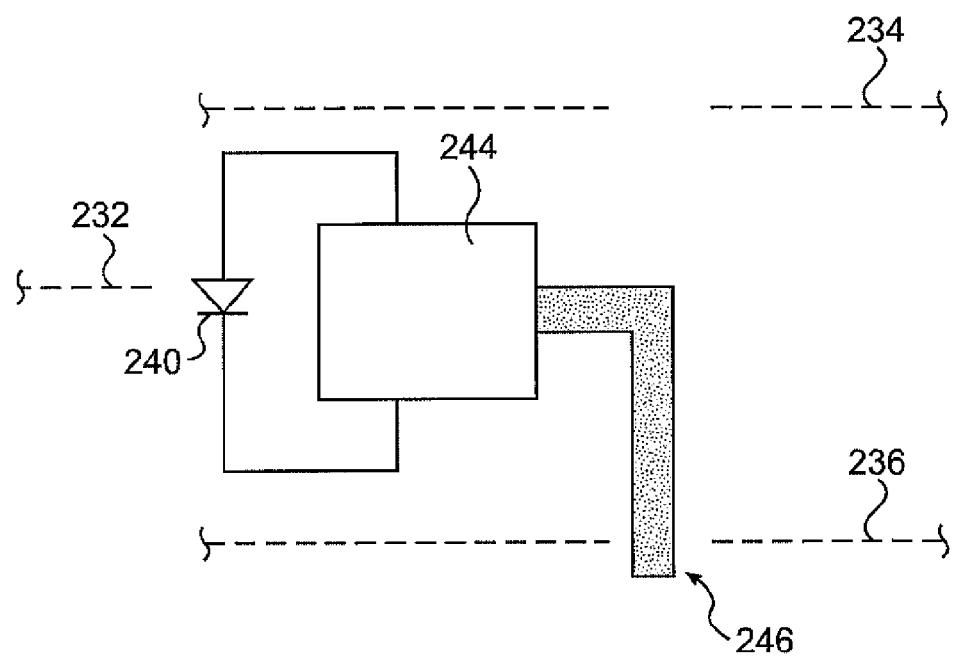

FIGS. 9(A) and 9(B) disclose an embodiment in which aboveground source of light powers a downhole galvanometer to operate a modulator in a one sampling channel and one reference channel configuration.

DETAILED DESCRIPTION

Context of the Invention

Figure 1:
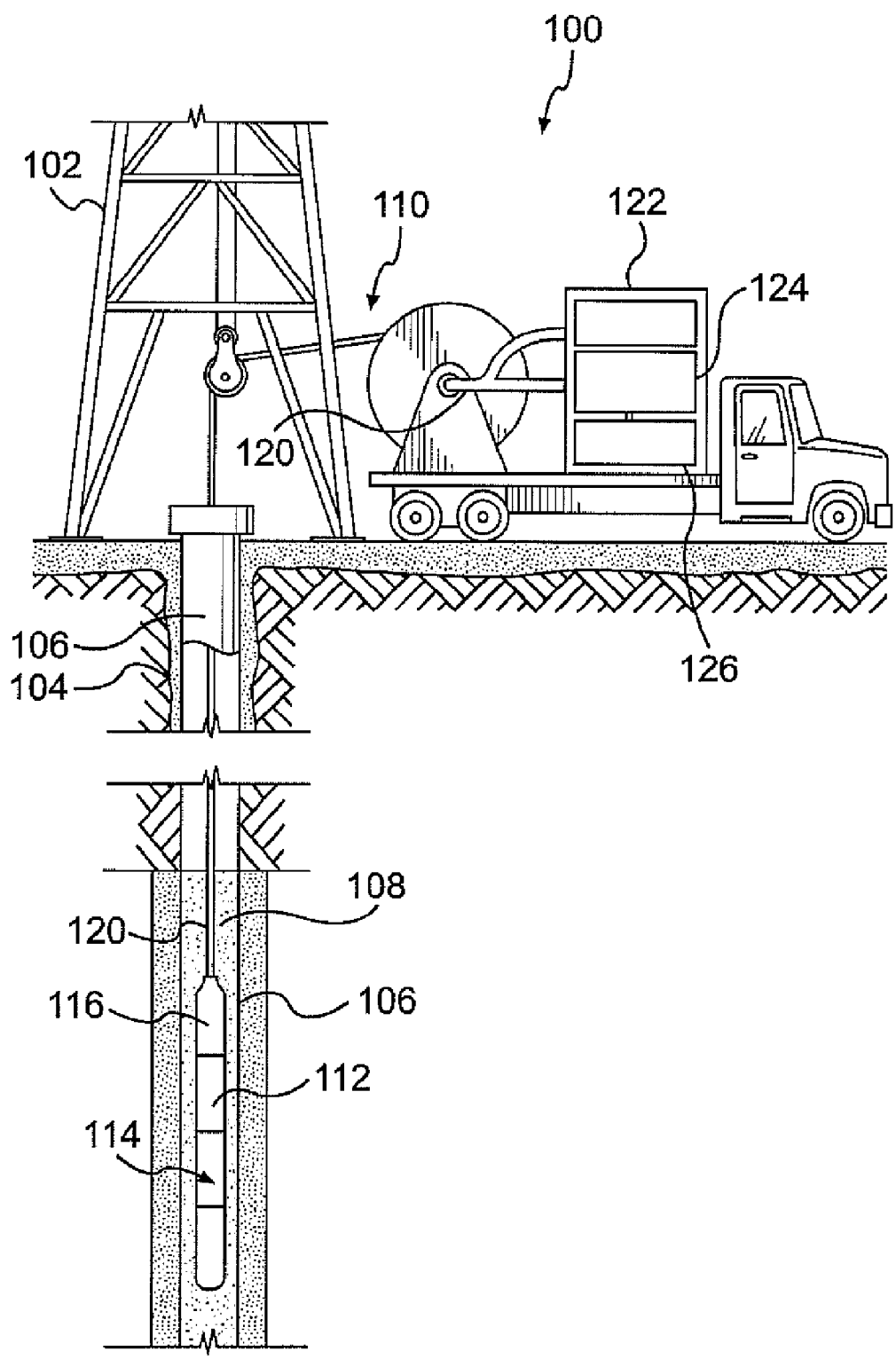
FIG. 1 is a representation of the system of the invention in the context of its application at an oil well site.

Turning now to the drawings wherein like numerals indicate like parts, FIG. 1 is a schematic of an oil well drilling system 100 illustrating an operative context of the invention. A conventional drilling derrick 102 is shown positioned above an oil well borehole 104. A casing 106 has been installed at the top of the borehole and cemented in place. The borehole may extend thousands of feet into the earth's crust, perhaps 25,000 feet, into an oil and/or gas bearing formation. Operational conditions at this depth may be twenty thousand pounds pressure per square inch and 150-175° C. in temperature.

Oil well logging managers are able to determine and map, on a real time and historic basis, vast amounts of well and formation data using oil well logging tools. A wire line cable 110 is connected to a logging tool 112 which has one or more sonde sections 114 and an instrumentation section 116. The logging tool is lowered into the wellhole 104 on the wireline 110 using techniques well known to those in the art. The sonde sections 114 are positioned within a formation zone 108 where fluids are to be sampled.

Fiber Optic In-Situ Fluids Sensing System

Figure 2:
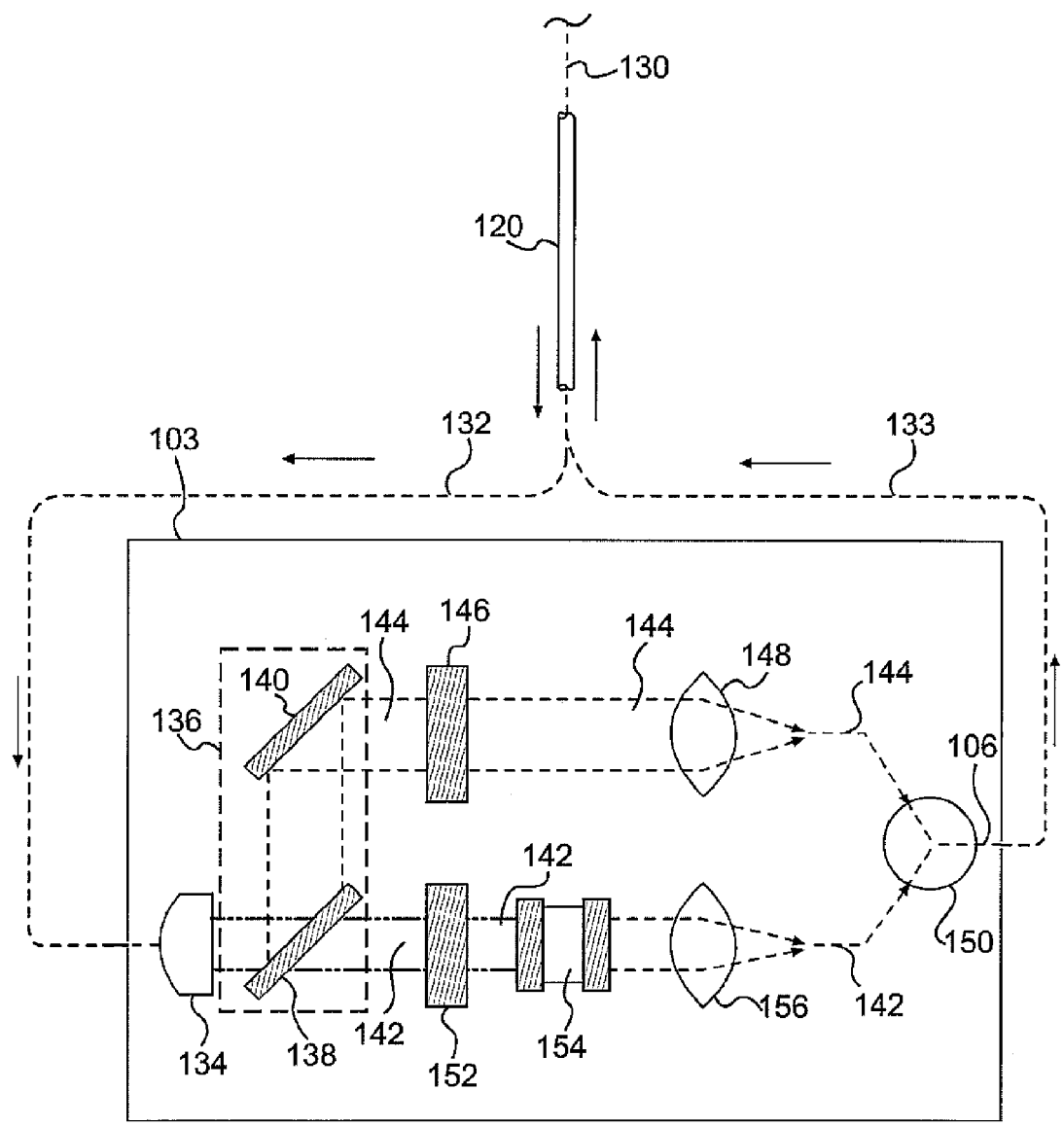
FIG. 2 depicts an embodiment of the invention in the case of a simple system employing one sample channel, one reference channel, and a single optical fiber.

Although real-time data can be transmitted between the logging tool cartridge 116 and the surface using an electrical line coupled with the wireline cable 110, in the subject invention, transmission is better accomplished with a fiber-optic cable 120 attached to the wireline 110. A steady, non-pulsed source of light 122 is connected to an optical fiber (not shown) within the cable 120. A detection system 124 and a signal processor 126 are located outside the well Within the logging tool, as shown in FIG. 2 in the case of a single sampling cell and single reference beam, an optical fiber 130 conducts the non-pulsed beam of light descending from its uphole source 122 and is directed through a segment of the fiber 132 to a collimating lens 134 which produces parallel rays of light. These parallel rays of light are directed through a splitter 136 which, by means of mirrors 138 and 140, separates the non-pulsed light into two beams, 142 and 144. One of the beams 144 is used as a reference and the other 142 is used for sampling the characteristics of reservoir fluids (not shown). The reference beam 144 is modulated by means of a mechanical chopper 146 and, after passing through a focusing lens 148 and a 2-to-1 optical coupler 150, is coupled with the sampling beam 142 to form a single return beam of multiplexed, non-pulsed light 133. The sampling beam 142 is also modulated by means of a mechanical chopper 152 and directed through an optical sampling cell 154 where wavelengths characteristic of the sample fluids are absorbed. After passing through a focusing lens 156, the sampling beam 142, is coupled with the reference beam in coupler 150. It will be appreciated by those familiar with the art, that there exist apparatus of varying sort to perform collimation, beam splitting, focusing and coupling. Furthermore, it will similarly be appreciated that multiplexing of the respective reference and sampling beams 144 and 142 can be performed with existing apparatus such as the Aritsu Laser gas detector marketed under model no. SA3C15A and that modulators for multiplexing the respective beams may be located at any place along the path of the split beams before they are coupled by coupler 150.

Downhole fluid sampling cells for optical work are also well known in the art, as for example those described by Yamate and Mullins in the Schlumberger '326 patent. Such sample cells capture samples of the system to be studied in the downhole conditions. Such systems include any physical systems that can alter the incoming light, either by a change of its amplitude (absorption measurement, for example) or by a change of its wavelength (fluorescence phenomenon, for example). The sampled systems may involve those whose measured characteristics are either stationary, i.e., constant with time, or dynamic, i.e., changing with time.

Modulation is used to apply onto the reference and sampling beams modulation schemes to carry the signals and further make it possible to distinguish between them when they are recombined onto the optical cable to be sent to the surface. Many different techniques may be applied to do so, such as phase modulation, frequency modulation, or by applying different modulation frequencies to each beam. Another use of modulation is to transmit information not necessarily related to properties of the sampled fluids. Such secondary information can be related to any system in the well tool that can interface with the modulator, such as those that measure ambient temperatures and pressures.

Although the modulator shown in the embodiment depicted in FIG. 2 is a mechanical chopper, the invention is not so limited. Other devices known in the art are available for modulation, the only requirement being that such devices withstand the frequently harsh environment (heat, pressure and other conditions) of oil field wellhole applications.

The recombined light from the sampling and reference optical paths are sent back to the surface on the single optical fiber 130 within the optical cable 120. The downhole data is then demodulated and the data inherent in its optical signals are processed by means known in the art. This may include, for example, conversion of the spectroscopic data from optical to electrical signals. The choice of optical detector will depend on the type of light source used at the surface. For example, if the light source is a narrow-wavelength tunable type, spectroscopy is performed directly by changing the source wavelength. In such cases, the detector does not have to be highly wavelength-selective and does not perform optical signal processing. It can be, for example, a photodiode type. If, however, the light source is broadband, then a wavelength selective receiver is desirable, such as a spectrometer associated with a broadband detector. The aboveground spectrometer performs optical signal processing by performing a spectral separation of the optical signals. This is accomplished by first transforming the optical signal into an electrical signal through the use of photodiodes. The resulting electrical signal generated at the output of the receiver can be processed to separate the contributions from the different channels.

The type of signal processing depends on the modulation scheme applied downhole for discriminating between the channels. Examples of applications for absorption spectroscopy for wireline include applications based on narrow band sources. FIG. 2 gives an example of some possible implementations in the case of a one-sample channel one-reference channel configuration with a narrow band source. This configuration is based on the use of a multi-frequency modulation scheme to differentiate between the channels.

One application of the described system is absorption spectroscopy to determine chemical compositions of the in-situ fluids. The system uses a light source located at the surface. It can be, for example, a laser device. One possible implementation for absorption spectroscopy applications uses a tunable laser. Wavelength tunable lasers are efficient, high power light sources of high spectral purity. By changing the wavelength it is possible to perform absorption spectroscopy measurements across a tuning range of the laser.

In addition to the attenuation of the signal resulting from absorption, attenuation of the light occurs by virtue of its passage downward from the light source to the splitter, through the modulators and in the return path to the surface. For accurate analytical determinations of the sampled characteristics, it is necessary to compensate or correct for the latter source of signal attenuation.

Such compensation may be demonstrated in the simple case depicted in FIG. 2. At the surface, the combined signal is composed of the reference signal and the sample signal. The light intensity of the sample signal arriving at the detector is given by:

$$I_{sample(t)} = K_{sample} * I_o * Att_1 * Att_{sample(t)} * Att_2 \quad (Eq. 1)$$

Where,
$I_{sample(t)}$=light intensity of sample channel
$K_{sample}$=fraction of Io split by beam splitter into sample channel
$I_o$=light intensity at light source input to above-surface fiber
$Att_1$=optical attenuation between light source at input and beam splitter on the sample channel
$Att_{sample(t)}$=optical attenuation of sample channel between beam splitter and optical coupler
$Att_2$=optical attenuation between optical coupler and above-surface detector The intensity of the reference signal arriving at the aboveground detector is given by:

$$I_{reference} = K_{reference} * I_o * Att_1 * Att_{reference(t)} * Att_2 \quad (Eq. 2)$$

Where,
$I_{reference(t)}$=light intensity of reference channel
$K_{reference}$=fraction of Io split by beam splitter into reference channel ($K_{sample}+K_{ref}\approx 1$)
$Att_{reference(t)}$=optical attenuation between beam splitter and optical coupler on the reference channel At the surface detector, the optical signal is converted to an electrical signal. The Fourier spectrum of the electrical signal will be the same as the optical signal as explained in FIGS. 4 and 5. For the sample channel, the amplitude of the light absorption can be retrieved by synchronous demodulation at $f_{sample}$. If the phenomenon is not stationary, it leads to an electrical signal in which:

$V_{sample(t)}$ proportional to: $I_{sample}$ where,
$V_{sample(t)}$=voltage of sample signal
The same demodulation can be performed for the reference channel, giving:

$V_{reference(t)}$ proportional to: $I_{reference}$

It is then possible to determine sample attenuation directly, without the need to take into account the attenuation experienced in the optical fiber, by calculating the ratio:

$$(V_{sample(t)}/V_{reference(t)}) = (K_{sample}/K_{reference})(Att_{sample(t)}/Att_{reference(t)})$$

Calibration of the system permits an a priori determination of $$(K_{sample}/K_{reference})/(Att_{reference(t)}),$$

as a result of which $Att_{sample}$ is directly determinable.

Spectroscopy can then be performed by changing the laser wavelength.

Figure 3:
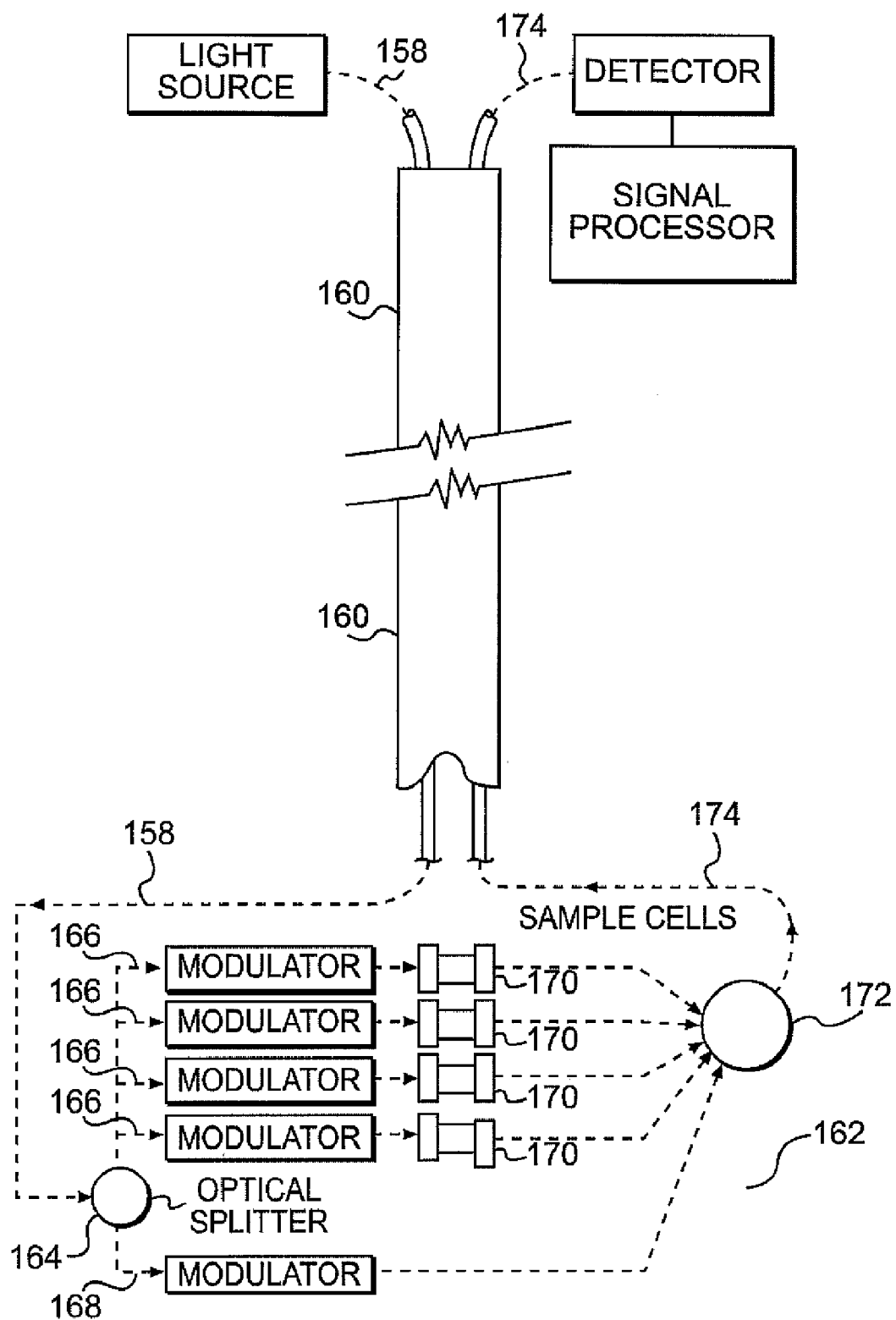
FIG. 3 shows schematically an application of the system utilizing multiple sampling cells and an optical path utilizing an optical cable with two optical fibers.

In the two-fiber optical cable configuration depicted in FIG. 3, one fiber 158 within the optical cable 160 is coupled to a laser light source and is used to send light from the surface to the sampling zone 162 of the wellhole. The fiber output is then coupled to a beam splitter 164. The beam splitter separates the light beam into "K" sampling beams, also referred to as sampling channels (in the embodiment depicted in FIG. 3, K=4) and "M" reference beams, also referred to as reference channels (in the embodiment depicted in FIG. 3, M=1). Mechanical choppers, or other types of modulators, are placed on each of the sampling 166 and reference 168 channels in order to create a modulation at a frequency $f_S$ and $f_M$. Light of the sampling channels is passed through the sampling cells 170 and is absorbed by the fluids contained in the cells (not shown), which fluids, in turn, have been collected from ambient fluids in the sampling zone. The absorption characteristics of these sampled fluids are, of course, a function of their chemical components. If, as is usually the case with fluids in oil wells, chemical and physical properties may be a dynamic function—i.e., changing over time—absorption will also be dynamic, and data from sampling channels will vary over time. In that case, the signals carried on the modulated sample channel will contain the Fourier transform of the optical signal. It is also envisioned that the composition or characteristic to be studied in the sampled fluids may be time invariant, i.e., static or stationary.

Figure 4:
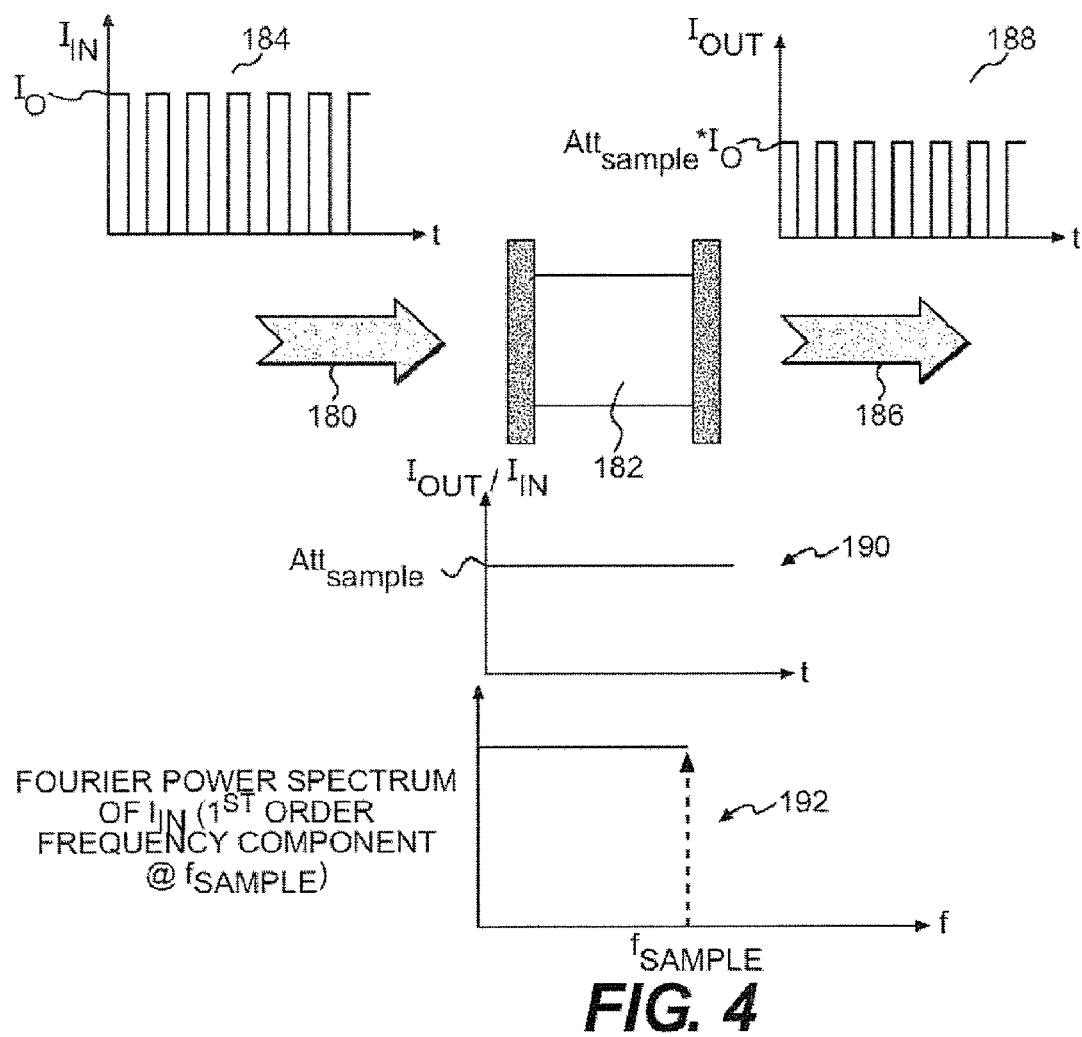
FIG. 4 is an embodiment of the invention employing optical signal modulation and stationary absorption measurement.

FIG. 4 depicts the case of a stationary sample where absorption is constant over time. The sampling channel of light 180 entering the sampling cell 182 has been modulated to a frequency $f_{sample}$, as reflected in the wave form of the light shown in the amplitude-time domain diagram 184. In traversing the sampling channel light 180 undergoes absorption from the fluid contained in the sampling cell, emerging with lowered amplitude resulting from the absorption. The amplitude-time domain of the emerging sampling channel beam 186 is reflected in 188. The amplitude of 186 is the product of the attenuation, $Att_{sample}$, times the amplitude of the entering beam 180. Since the sampled fluid is invariant with time, the attenuation is also invariant, as reflected in 190. The frequency view is also shown in the FIG. 4. The Fourier power spectrum will likewise be invariant 192.

Figure 5:
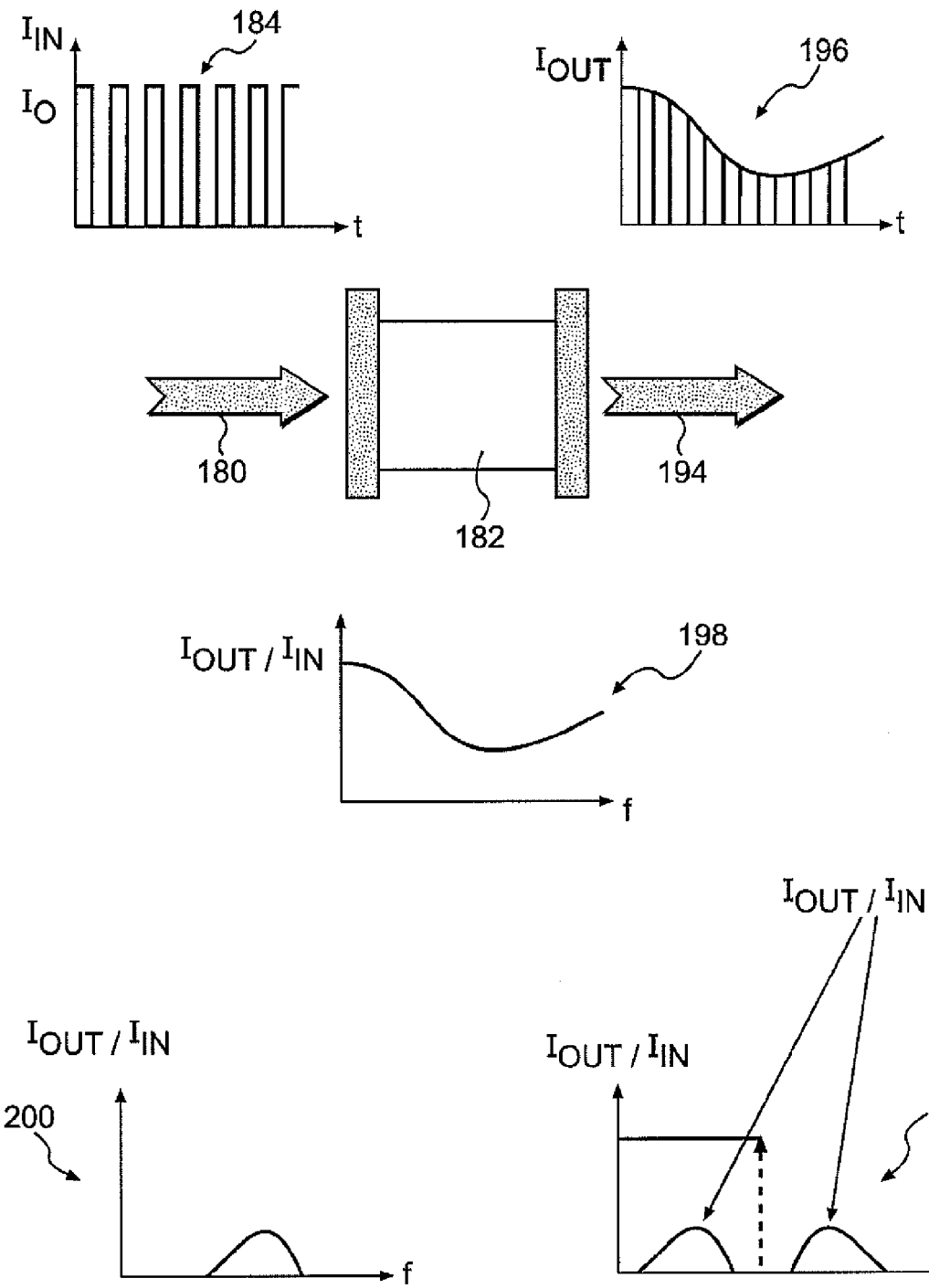
FIG. 5 is an exemplary embodiment of the invention employing optical signal modulation and dynamic absorption measurement.

FIG. 5 depicts the form of optical signals in the case of fluid samples whose chemical composition vary over time. The sampling channel light 180 entering the sample cell 182 with the same modulation scheme as in the stationary case of FIG. 4 emerges 194 from the sample cell with an attenuation which varies in time with the changing composition of the sampling cell fluid. An illustrative example of the time domain plot of the sampling channel light after absorption is shown 196. A plot of the absorption, which is $I_{OUT}/I_{IN}$ (t) is depicted in 198. A Fourier power spectrum of the attenuation of the sampling channel light 194 is reflected in 200. As in electrical or electromagnetic communications applications, the modulation frequency is used as a carrier frequency and the information is carried on the sidebands of the main frequency peak centered on $f_{sample}$. Thus, where the signal process is performed by lock-in at the sample beam frequency $f_{sample}$, the temporal shape of $I_{OUT}/I_{IN}$ (t) the first order frequency component Fourier power spectrum for the sample under discussion is depicted in plot 202.

In FIG. 3, after the sampling channels pass through the sampling cells 170, they, together with the reference channel, are combined by means of an optical coupler 172, and the resultant signal is directed above ground through a second optical fiber 174. There, the optical signal is detected, demodulated and passed to a signal processor from which the characteristics from the sampled cells may be analyzed.

Figure 6:
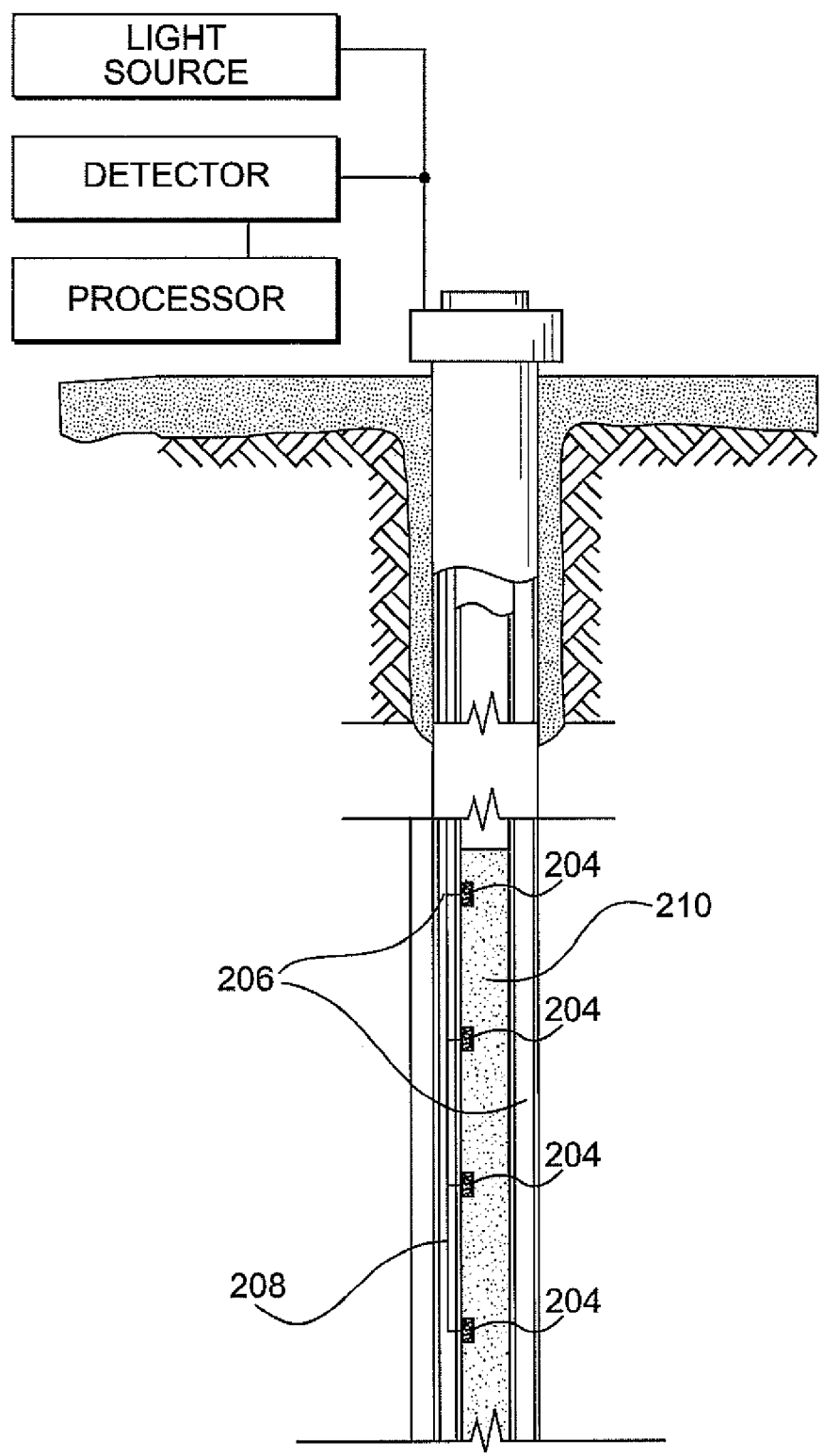
FIG. 6 shows sampling cells employed at fixed locations within the wellhole.

Sampling of wellhole fluids is not restricted to sampling cells within a sonde. If continuous testing or analysis is desired from fixed locations within the wellhole, sampling cells 204 may placed in fixed locations, as is illustrated in FIG. 6. Other components of the invention, such as beam splitters, modulators, optical couplers (not shown) may be deployed within casing annulus 206 at nodes along the optical fiber 208, or within the casing itself 210.

Applications with broad-band sources, including all light sources with a broadband emission spectrum, may use the same architecture. However, in order to perform spectroscopic analysis, a spectrometer is required. One appropriate type spectrometer is a grating spectrometer associated with a photodiode array. Each pixel j of the photodiode array is associated to one central wavelength $\lambda_j$. Then, the demodulation scheme disclosed above for narrow-band sources can be applied to each of the pixels. It is thereby possible to determine the attenuation on each pixel. From such measurements it is possible to evaluate the absorption spectrum of the sample.

Another aspect of the invention includes ways to provide energy to power devices used for modulation of light and to implement the modulation scheme. One way of powering devices located downhole is to use electrical power transmitted downhole through an electrical cable. In some applications, as, for example, permanent downhole monitoring, electrical power may not be available downhole. However, where such power is unavailable or impractical due to wellhole conditions in the sampling zone, the optical energy transmitted through the optical cable may also be employed to provide downhole power. Part of the energy of the light transmitted through the optical fibers within the cable can be used for the implementation of different modulation schemes. To do so, part of the light transmitted through the cable is diverted to a driver that is used to drive the modulators. The driver is a device that converts the energy provided by the light traveling through the cable into a signal that can be used to drive the light modulator.

Figure 7:
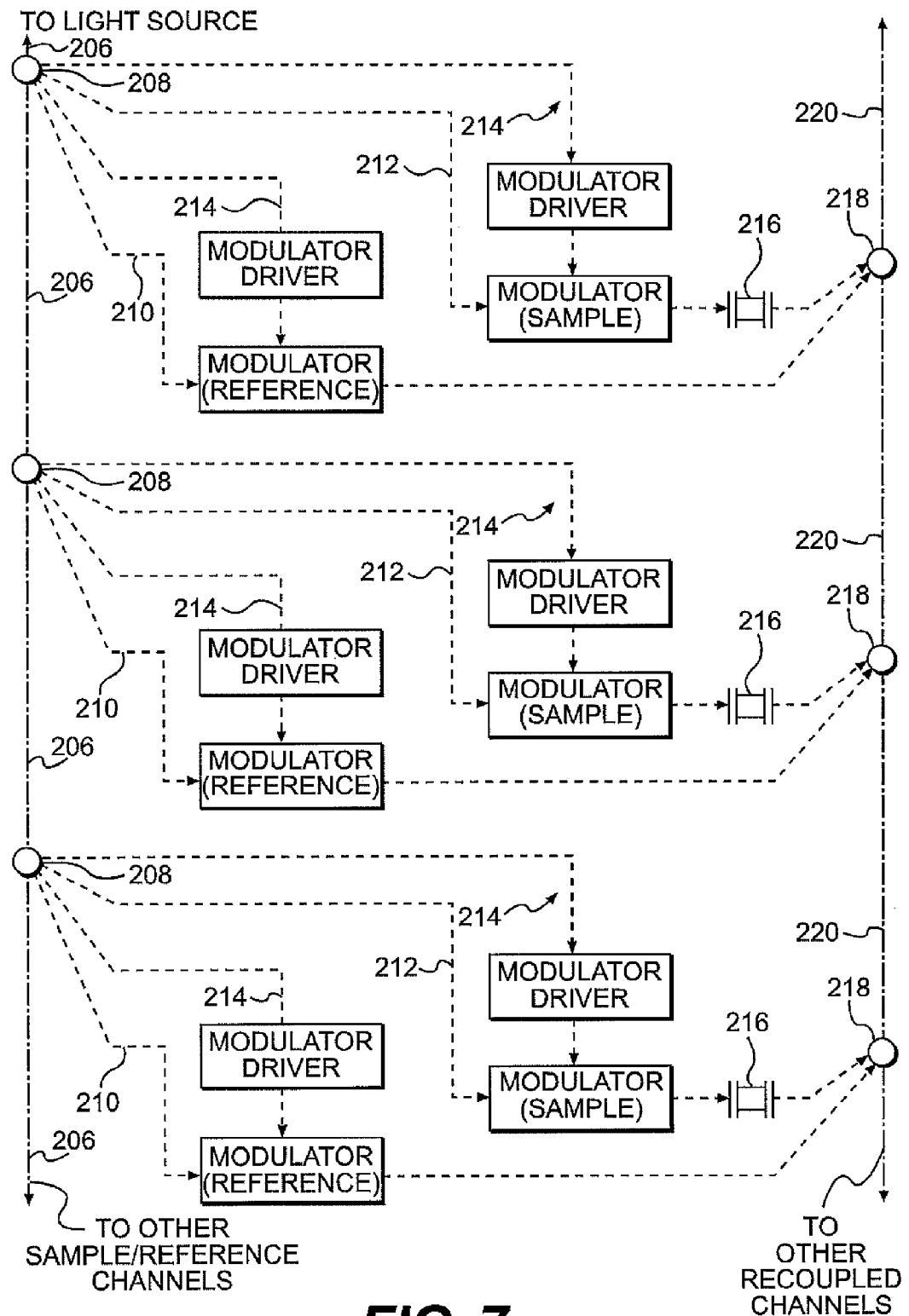
FIG. 7 illustrates an exemplary embodiment of the invention in which optical cables are used to power modulators.

This is illustrated in FIG. 7. The optical fiber 206 connected to the light source outside the well (not shown) is connected to optical splitters 208 along the length of the optical fiber within the sampling zone, in the case of fixed sampling cells, or within the sonde, in the case of a wireline probe. The splitters create separate channels used for reference channels 210, sampling channels 212, and channels 214 used for powering modulators. As previously described, modulated sampling channels are directed through sampling cells 216, re-coupled by optical couplers 218 and either directed through a second optical fiber 218 (in a two optical fiber configuration) for transmission to the above-ground signal detector or returned to the single optical fiber (in a single wire configuration) (not shown) for detection and processing.

Channels 214 for powering modulators are directed to photodiodes that convert the optical power into an electrical signal. The output of the photodiode is connected to a self-oscillating circuit. One way of implementing such a circuit is by using a structure such as an LC oscillator. The oscillator is tuned to an oscillation frequency $(f_{osc})_j$. The oscillator output is then connected to the modulator. In the present case, an inline modulator such as that described above, may be preferable to a chopper motor, since they are usually low power devices. An additional advantage is that inline modulators can provide light modulation directly proportional to the voltage applied to their input. Therefore, in this case, light intensity is directly modulated at $(f_{osc})_j$.

FIG. 8 depicts an embodiment of a one-sample-cell configuration. Light arriving downhole on the optical fiber 222 is split into four channels by the optical splitter 224. Two of the channels 226 are directed to the photodiode detectors 228 which convert the photo energy to electricity, which is directed through electrical conductors 230 to LC oscillator circuits to drive a sample channel modulator tuned to $(f_{osc})_{sample}$ and reference channel modulator tuned to $(f_{osc})_{ref}$.

FIGS. 9(A) and 9(B) show a further embodiment of the invention in which a galvanometer functions as a downhole optical path switch to direct light from the aboveground source through downhole optical fiber paths. Incoming light 232 from aboveground is turned on and off to operate a galvanometer which acts as a shutter or modulator. In FIG. 9(A), when the light is on 242, it is directed to a photodiode 240 which generates electrical current. This current is connected to the coil (not shown) of the galvanometer 244, which in its energized state operates a shutter. In the case illustrated, the shutter is in a position 238 that blocks light in the reference channel 234. When the light is off (illustrated in FIG. 9(B)), no power is produced by the photodiode, which, in turn places the shutter in a position 246 that blocks light in the sampling channel.

The operation of such a modulator requires power produced with a few milliamps at voltages of the order of 0.1 volts. Photodiodes can typically produce such power. The use of such a galvanometer may be preferable to an optical switch which typically requires 100 ma at 5 volts for its operation.

The various aspects of the invention were chosen and described in order to best explain principles of the invention and its practical applications. The preceding description is intended to enable those of skill in the art to best utilize the invention in various embodiments and aspects and with modifications as are suited to the particular use contemplated. It is intended that the scope of the invention be defined by the following claims.

What is claimed is:

1. A system configured with enhanced attenuation compensation for optically sampling characteristics of subsurface fluids within a wellhole, said system comprising:
   a source of light located outside a well;
   at least one optical fiber connected to said source of light for transmission of light to an operative location within the wellhole;
   at least one optical splitter connected to said optical fiber within said wellhole for splitting the beam of light into at least two channels of light, constituting at least one sampling channel and at least one reference channel, wherein the at least one sampling channel is as long as the at least one reference channel;
   a modulator connected downstream of said optical splitter to each of said at least one reference channel for modulating the light of each reference channel to which such modulator is connected;
   a modulator connected downstream of said optical splitter to each of said at least one sampling channel for modulating the light of each sampling channel to which such modulator is connected;
   an optical-to-electrical converter to power a galvanometer with light transmitted downhole though said optical fiber for switching light transmission in each channel;
   at least one wellhole fluids sampling cell operable to be positioned within the wellhole and connected to said at least one sampling channel within the wellhole;
   at least one optical coupler for joining light from said at least one sampling channel and said at least one reference channel and inputting said light into at least one optical fiber for return of information to the surface of said wellhole for analysis; and
   a signal detector and processor located outside the well and being connected to said optical fiber for analyzing signals received from said at least one fluids sampling cell and said at least one reference channel,
   said system having enhanced attenuation compensation based on a ratio of the signals received from the at least one wellhole fluids sampling cell and said at least one reference channel, a fraction ratio in splitting the beam of light into the at least two channels of light, and an optical attenuation between the at least one optical splitter and the at least one optical coupler.

2. A system as defined in claim 1, wherein said source of light comprises:
   a continuous laser source of light energy.

3. A system as defined in claim 1, wherein:
   said at least one optical fiber is a single optical fiber within an optical cable.

4. A system as defined in claim 1, wherein:
   said modulator connected to said at least one sampling channel is connected upstream of the sampling cell in said channel.

5. A system as defined in claim 1, wherein:
   said modulator connected to said at least one sampling channel is connected downstream of the sampling cell in said channel.

6. A system as defined in claim 1, wherein:
   the at least one sampling channel comprises a plurality of sampling channels.

7. A system as defined in claim 6, wherein:
   the optical splitter being connected to said optical fiber within said wellhole for splitting the beam of light into a plurality of channels of light, constituting four sampling channels and one reference channel.

8. A system configured with enhanced attenuation compensation for optically sampling characteristics of subsurface fluids within a wellhole, wherein said system comprises:
   a continuous laser source of light energy located above a well;
   a single optical fiber connected to said source of laser light and operable for transmission of light to an operative location within the wellhole;
   at least one optical splitter connected to said optical fiber within said wellhole for splitting the beam of laser light into at least two channels of light, constituting a plurality of sampling channels and at least one reference channel, wherein the at least one sampling channel is as long as the at least one reference channel;
   a modulator connected downstream of said optical splitter to each of said at least one reference channel;
   a modulator connected downstream of said optical splitter to each of said plurality of sampling channels between at least one of the optical splitter and the sampling cell and between the sampling cell and an optical coupler;
   an optical-to-electrical converter to power a galvanometer with light transmitted downhole through said optical fiber for switching light transmission in each channel;
   at least one wellhole fluids sampling cell operable to be positioned within the wellhole and connected to each of said plurality of sampling channels within the wellhole;
   at least one optical coupler for joining light from said plurality of sampling channels and said at least one reference channel and inputting said light into said single optical fiber for return of information to the surface of said wellhole for analysis; and
   a signal processor located outside the well and being connected to said optical fiber for analyzing signals received from the plurality of fluid sampling cell and said at least one reference channel, wherein:
   said system is configured with enhanced attenuation compensation based on a ratio of the signals received from the at least one wellhole fluids sampling cell and said at least one reference channel, a fraction ratio in splitting the beam of light into the at least two channels of light, and an optical attenuation between the at least one optical splitter and the at least one optical coupler.

9. A method for optically sampling characteristics of subsurface fluids within a wellhole with enhanced attenuation compensation, said method comprising the steps of:
   providing a source of light above the surface of a wellhole;
   transmitting the light within at least one optical fiber into a wellhole to a zone within said wellhole for use in sampling fluids;
   splitting the light into at least one sampling channel of light and at least one reference channel of light within the wellhole, wherein the at least one sampling channel is as long as the at least one reference channel;
   modulating the light of the at least one sampling channel and the light of the at least one reference channel;
   employing an optical-to-electrical converter with light transmitted downhole though said optical fiber to power a galvanometer for switching light transmission in each channel;
   transmitting the at least one sampling channel through a fluid sample cell within the wellhole;
   coupling said at least one sampling channel and said at least one reference channel;
   transmitting the coupled channels through the optical fiber to the surface of the wellhole for analysis;

analyzing signals received from the fluid sample cell and said at least one reference channel; and compensating for attenuation based on the signals received from the fluid sample cell and said at least one reference channel.

10. A method as defined in claim 9, wherein said method further comprises the steps of:

providing a signal detector and processor located outside the well and connected to the optical fiber.

11. A method as defined in claim 9, wherein said step of providing a source of light comprises:

providing a source of laser light that emits continuous light energy.

12. A method as defined in claim 9, wherein the step of transmitting the light within at least one optical fiber comprises:

transmitting the light through a single optical fiber.

13. A method as defined in claim 9, wherein said step of modulating the light of the at least one sample channel and the step of transmitting the at least one sampling channel through a fluid sample cell within the wellhole comprises:

modulating a plurality of sampling channels and transmitting each sampling channel through a sample cell associated therewith.

14. A method as defined in claim 9, wherein said method further comprises the step of:

modulating a plurality of reference channels.

15. A method as defined in claim 9, wherein said step of modulating the at least one sampling channel comprises:

placing a modulator upstream of the sample cell.

16. A method as defined in claim 9, wherein said step of modulating the at least one sampling channel comprises:

placing a modulator downstream of the sample cell.

17. A method as defined in claim 9, wherein said method further comprises the steps of:

providing a signal detector and processor located outside the well and connected to the optical fiber;

providing as the source of light a laser that emits continuous light energy; and transmitting the light through a single optical fiber.

18. A method as defined in claim 9, wherein the step of splitting the light comprises:

splitting the source of light into at least four sampling channels and at least one reference channel and the step of modulating comprises modulating the at least four sampling channels and the at least one reference channel.

19. A method as defined in claim 18, wherein the step of modulating at least four sampling channels comprises:

placing a modulator on at least one of the at least four sampling channels upstream of the sample cell associated therewith and placing a modulator on each remaining sampling channels downstream of the sample cell associated therewith.

* * * * *